US00PP26514P3

(12) United States Plant Patent
Trees

(10) Patent No.: US PP26,514 P3
(45) Date of Patent: Mar. 15, 2016

(54) ***AGASTACHE* PLANT NAMED 'LITTLE ADDER'**

(50) Latin Name: *Agastache rugosa*
Varietal Denomination: Little Adder

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 80 days.

(21) Appl. No.: 14/121,129

(22) Filed: Aug. 4, 2014

(65) Prior Publication Data

US 2016/0037698 P1 Feb. 4, 2016

(51) Int. Cl.
*A01H 5/02* (2006.01)

(52) U.S. Cl.
USPC ..... Plt./399

(58) Field of Classification Search
USPC ..... Plt./399
CPC ..... A01H 5/02; A01H 5/00
See application file for complete search history.

*Primary Examiner* — Kent L Bell
(74) *Attorney, Agent, or Firm* — Audrey Charles

(57) ABSTRACT

A new and distinct cultivar of *Agastache* plant named 'Little Adder', characterized by its medium violet-colored flowers, dark green-colored foliage, and moderately vigorous, upright-mounded growth habit, is disclosed.

1 Drawing Sheet

Latin name of genus and species of plant claimed: *Agastache rugosa.*
Variety denomination: 'Little Adder'.

BACKGROUND OF THE INVENTION

The present invention relates to a new and distinct cultivar of *Agastache* plant botanically known as *Agastache rugosa* and hereinafter referred to by the cultivar name 'Little Adder'.

The new cultivar originated in a controlled breeding program in Guadalupe, Calif. during the summer of 2011. The objective of the breeding program was the development of *Agastache* cultivars having a more compact and better-branched growth habit.

The new *Agastache* cultivar is the result of open-pollination. The female (seed) parent of the new cultivar is 'Heronswood Strain', not patented, characterized by its medium violet-colored flowers, dark green-colored foliage, and vigorous, upright growth habit. The male (pollen) parent of the new cultivar is unknown. The new cultivar was discovered and selected as a single flowering plant within the progeny of the above stated open-pollination during September 2011 in a controlled environment in Guadalupe, Calif.

Asexual reproduction of the new cultivar by terminal stem cuttings since September 2011 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Little Adder' as a new and distinct cultivar of *Agastache* plant:

1. Medium violet-colored flowers;
2. Dark green-colored foliage; and
3. Moderately vigorous, upright-mounded growth habit.

Plants of the new cultivar differ from plants of the female parent primarily in having a less vigorous and more mounded growth habit.

Of the many commercially available *Agastache* cultivars, the most similar in comparison to the new cultivar is 'Black Adder', not patented. However, in side by side comparisons, plants of the new cultivar differ from plants of 'Black Adder' in at least the following characteristics:

1. Plants of the new cultivar are shorter than plants of 'Black Adder'; and
2. Plants of the new cultivar are better-branched than plants of 'Black Adder'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Little Adder'. The plants were grown in one-gallon containers for approximately two months in a greenhouse and one month outdoors in Elburn, Ill. Plants were given one pinch prior to transplant and one pinch two weeks after transplant.

DETAILED BOTANICAL DESCRIPTION

Figure 1:
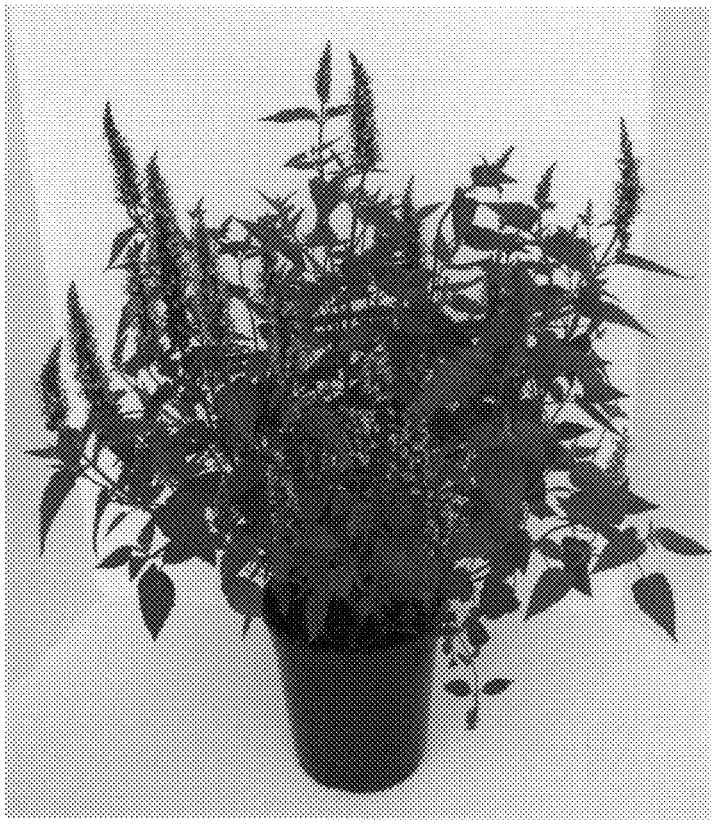
FIG. 1 illustrates a side view of the overall growth and flowering habit of 'Little Adder'.
Figure 2:
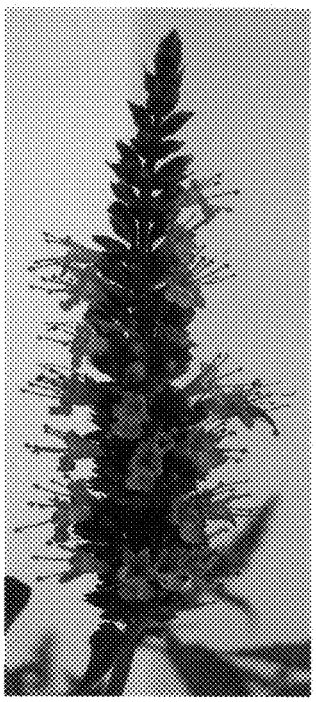
FIG. 2 illustrates a close-up view of an individual inflorescence of 'Little Adder'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2014 under natural light conditions in West Chicago, Ill.

The following descriptions and measurements describe plants produced from cuttings from stock plants and grown under conditions comparable to those used in commercial practice. The plants were grown utilizing a soilless growth medium in one-gallon containers for approximately two months in a greenhouse and one month outdoors in Elburn, Ill. Plants were given one pinch prior to transplant and one pinch two weeks after transplant. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Agastache rugosa* cultivar Little Adder.

Parentage:

*Female parent*.—'Heronswood Strain', not patented.

*Male parent*.—Unknown.

Propagation:

*Type cutting*.—Terminal stem.

*Time to initiate roots*.—Approximately 10 to 12 days.

*Time to produce a rooted cutting*.—Approximately 5 weeks.

*Root description*.—Fine, fibrous, white in color.

*Rooting habit*.—Freely branching.

Plant description:

*Commercial crop time*.—Approximately 10 to 12 weeks from a rooted cutting to finish in a 15 cm pot.

*Growth habit and general appearance*.—Moderately vigorous, upright-mounded.

*Size*.—Height from soil level to top of plant plane: Approximately 53.0 cm. Width: Approximately 51.0 cm.

*Branching habit*.—Freely branching. Pinching enhances lateral branching. Quantity of branches per plant: Approximately 4 main basal branches with laterals forming at each node.

*Lateral branch*.—Shape: Square in cross section. Strength: Strong. Length to base of inflorescence: Approximately 34.0 cm. Diameter: Approximately 4.0 mm. Length of central internode: Approximately 5.5 cm. Texture: Sparsely pubescent. Color of young and mature stems: 146B tinted 187A from sun.

Foliage description:

*General description*.—Quantity of leaves per branch: Approximately 10. Fragrance: Strong, sage-like. Form: Simple. Arrangement: Opposite.

*Leaves*.—Aspect: Petiole at acute to perpendicular angle to stem, blade perpendicular to obtuse angle to stem. Shape: Ovate. Margin: Crenate. Apex: Acute. Base: Cordate. Venation pattern: Pinnate. Length of mature leaf: Approximately 5.2 cm. Width of mature leaf: Approximately 3.1 cm. Texture of upper surface: Rugous, sparsely pubescent. Texture of lower surface: Rugous, densely pubescent on venation. Color of upper surface of young and mature foliage: 137A with venation of 146B. Color of lower surface of young and mature foliage: Closest to 137C with venation of 146D.

*Petiole*.—Length: Approximately 2.7 cm. Diameter: Approximately 1.0 mm. Texture: Sparsely pubescent. Color: 146B tinted 187A from sun.

Flowering description:

*Flowering habit*.—'Little Adder' is freely flowering under outdoor growing conditions blooming from late spring through autumn and with limited flowering under short winter days in a greenhouse environment.

*Lastingness of individual floret*.—Approximately 7 days.

Inflorescence description:

*General description*.—Type: Spikes in verticillaster arrangement, florets in clusters of approximately 10, not persistent. Quantity of inflorescences per plant: Approximately 29. Fragrance: None detected. Length or height of inflorescence: Approximately 11.0 cm. Width of inflorescence: Approximately 3.0 cm. Quantity of fully-open flowers per inflorescence: Approximately 55, typically 2 to 3 florets per verticillaster open over time.

*Peduncle*.—Shape: Square in cross section. Strength: Strong. Aspect: Erect. Length: Approximately 3.0 cm. Diameter: Approximately 2.0 to 3.0 mm. Texture: Sparsely pubescent. Color: 146B.

Flower description:

*Type*.—Single, zygomorphic.

*Bud just before opening*.—Shape: Obovoid. Length: Approximately 5.0 mm. Diameter: Approximately 2.0 mm. Texture: Densely glandular pubescent. Gland color: Colorless, transparent. Color: Calyx of 146C with venation of 187A and tips of N88A; petals of N88B with N88C.

*Corolla*.—Shape: Bilabiate, five lobes arranged as two upper lobes, and one three-lobed lower lip. Width: Approximately 4.0 mm. Length: Approximately 5.0 mm. Depth: Approximately 1.2 cm.

*Upper lobes*.—Shape: Oblong. Margin: Entire. Apex: Rounded. Length from throat: Approximately 1.0 mm. Width: Approximately 1.0 mm. Texture of inner surface: Glabrous. Texture of outer surface: Densely pubescent. Color of inner surface when first and fully open: N88C. Color of outer surface when first and fully open: N88D to N88C.

*Lower lip*.—Shape of central lobe: Obovate. Shape of lateral lobes: Oblong, curved toward central lobe. Margin of all lobes: Entire. Apex of central lobe: Praemorse. Apex of lateral lobes: Rounded. Length from throat of central lobe: Approximately 2.0 mm. Width of central lobe: Approximately 4.0 mm. Length from throat of lateral lobes: Approximately 1.0 mm. Width of lateral lobes: Approximately 1.0 mm. Texture of upper surface: Glabrous, with central lobe having a densely pubescent patch at tube opening. Texture of lower surface: Densely pubescent. Color of upper surface when first and fully open: N88C. Color of lower surface when first and fully open: N88D to N88C.

*Calyx*.—Shape: Tubular. Length: Approximately 5.0 mm. Diameter: Approximately 2.5 mm.

*Sepals*.—Quantity per flower: 5, fused. Shape: Elliptic. Apex: Acute. Length: Approximately 5.0 mm. Width: Approximately 1.0 mm. Texture of inner surface: Glabrous. Texture of outer surface: Densely glandular pubescent. Gland color: Colorless, transparent. Color of inner surface: 146B with a heavy overlay of N186A and margins of N88A. Color of outer surface: 146D with a heavy overlay of N186A and margins of N88A.

*Bracts*.—Quantity: One bract located at the base of floret cluster. Texture of upper surface: Glabrous. Texture of lower surface: Densely pubescent. Color of upper surface: 146B. Color of lower surface: 146D.

*Pedicel*.—Strength: Strong, flexible. Aspect: At an acute angle. Length: Approximately 1.0 mm to 2.0 mm. Diameter: Less than 1.0 mm. Texture: Densely pubescent. Color: 146D tinted 187A from sun.

*Reproductive organs*.—Androecium: Stamen quantity: 4 per flower, adnate to corolla tube. Stamen length: Two pair approximately 1.1 cm and two pair approximately 1.2 cm. Filament length of fixed portion: Approximately 4.0 mm. Filament color: 90B to 90C. Anther shape: Bi-lobed. Anther length: Less than 1.0 mm. Anther color: 86B. Pollen amount: Moderate. Pollen color: NN155D. Gynoecium: Pistil quantity: 1 per flower. Pistil length: Approximately 1.3 cm. Stigma shape: Bi-parted. Stigma length: 1.0 mm. Stigma color: 90B. Style length: Approximately 1.1 cm. Style color: NN155D, opaque with a faint overlay of 90B that fades toward ovary. Ovary diameter: Approximately 1.0 mm. Ovary color: 144A.

Seed and fruit production: Neither seed nor fruit production has been observed.

Disease and pest resistance: Resistance to pathogens and pests common to *Agastache* has not been observed.

What is claimed is:

1. A new and distinct cultivar of *Agastache* plant named 'Little Adder', substantially as herein illustrated and described.

* * * * *